United States Patent [19]

Wallace

[11] Patent Number: 4,767,700
[45] Date of Patent: Aug. 30, 1988

[54] DETECTION OF PARTICULAR NUCLEOTIDE SEQUENCES

[75] Inventor: R. Bruce Wallace, Freiburg, Fed. Rep. of Germany

[73] Assignee: Beckman Research Institute of the City of Hope, Duarte, Calif.

[21] Appl. No.: 702,099

[22] Filed: Feb. 15, 1985

[51] Int. Cl.$^4$ .............................................. C12Q 1/68
[52] U.S. Cl. ...................................... 435/6; 435/803; 935/78; 436/811
[58] Field of Search ...................... 435/6, 803; 935/78; 436/501, 811

[56] References Cited

U.S. PATENT DOCUMENTS 4,395,486  7/1986  Wilson et al. ...................... 435/7 X

OTHER PUBLICATIONS

Thein, S. L. et al., *In: Human Genetic Diseases a Practical Approach* (K. E. Davies, editor), IRL Press, Oxford, England, 1986, pp. 33–50.

Kennell, D. E., *In* Progress in Nucleic Acid Research and Molecular Biology (Davidson et al., ed.) vol. 11, 1971, Academic Press, N.Y., pp. 259–261.

Meinkoth, J. et al., *Anal. Biochem.*, vol. 138, 1984, pp. 267–269.

Singer-Sam, J. et al., *Proc. Natl. Acad. Sci. USA*, vol. 80, 1983, pp. 802–806.

Conner, B. J. et al., *Proc. Natl. Acad. Sci. USA*, vol. 80, 1983, pp. 278–282.

*Primary Examiner*—Charles F. Warren
*Assistant Examiner*—Jeremy M. Jay
*Attorney, Agent, or Firm*—Sprung Horn Kramer & Woods

[57] ABSTRACT

A process for the detection of a particular polynucleotide sequence in a polynucleotide-containing test sample comprising forming an agarose gel having a depression therein, adding the test sample to said depression, putting agarose solution in the depression and permitting it to gel thereby to encase the test sample in agarose gel, denaturing the polynucleotide in the test sample within the agarose gel, under hybridization conditions contacting the test sample-containing gel with an oligonucleotide or polynucleotide probe having a sequence complementary with a sequence for which the sample is being tested, and determining the extent of hybridization.

9 Claims, No Drawings

DETECTION OF PARTICULAR NUCLEOTIDE SEQUENCES

The present invention relates to a simplified process for testing an unknown sample of nucleic acid to determine the presence or absence of a particular nucleotide sequence.

It is known, for example, in Application Ser. No. 302,815, filed Sept. 16, 1981, now abandoned, to analyze an unknown nucleic acid for the presence or absence of a particular nucleotide sequence by determining the ability of the unknown to hybridize with a probe carrying a nucleotide sequence selectively complementary to the unknown nucleic acid or to a close variant thereof, the extent of hybridization indicating the presence of one or the other, i.e., normality or abnormality.

To obtain a readout of the extent of hybridization, the probe carried a readable label, e.g., radioactivity, biotin.

To prepare the unknown sample, it was treated with a restriction enzyme to form smaller fragments. The mixture of fragments was subjected to electrophoresis on a gel such as agarose, to separate the fragments which might hybridize from other portions of the nucleic acid which were not useful in the test, and the gel dried. The desired fraction was then subjected to hybridization conditions with a probe and the product assayed by reading the probe.

One of the problems with prior techniques as actually carried out was that the DNA of the unknown would trap oligonucleotides of the labelled probe as opposed to actually hybridizing specifically with them. Accordingly, the product after being subjected to hybridization conditions, would show labelled probe even if hybridization had not actually occurred. To prevent this false reading it was therefore necessary to subject the product to lengthy washing to remove any labelled probe which was not actually hybridized.

While this gives satisfactory results, it is slow and requires much skilled operator time.

It is accordingly an object of the present invention to provide a quicker, simpler and still reliable test for detecting the presence or absence of a particular polynucleotide sequence in a polynucleotide-containing test sample comprising forming an agarose gel having a depression therein, adding the test sample to said depression, putting agarose solution in the depression and permitting it to gel thereby to encase the test sample in agarose gel, denaturing the polynucleotide in the test sample within the agarose gel, under hybridization conditions contacting the test sample-containing gel with an oligonucleotide or polynucleotide probe having a sequence complementary with a sequence for which the sample is being tested, and determining the extent of hybridization. Advantageously the probe carries a readable label and the extent of hybridization is determined by reading the label. A suitable label is a radioactive isotope, biotin, and the like.

The test of the invention is thus designed to give an easy "read out" procedure for the diagnosis of particular genetic diseases using oligonucleotide or polynucleotide probes. Basically, the DNA in question is immobilized, and hybridized with either a probe for the mutant sequence (pmt) or a probe for the normal sequence (pwt). The pattern of hybridization then allows diagnosis as follows:

| probe | genotype | | |
|---|---|---|---|
| | wt/wt | wt/mt | mt/mt |
| pwt | ++ | + | − |
| pmt | − | + | ++ |

Using a probe for the normal sequence (pwt), the extent of hybridization will be greater when the genotype of the unknown sample is homozygous for the normal sequence (e.g., wt/wt) than when the genotype is heterozygous (e.g., wt/mt). When the genotype of the unknown is homozygous for the mutant sequence (e.g., mt/mt), no hybridization will occur.

In the same manner, using a probe for the mutant sequence (pmt), the extent of hybridization will be greater when the genotype of the unknown sample is homozygous for the mutant sequence (e.g., mt/mt) than when the genotype is heterozygous (e.g., wt/mt). In this case, no hybridization will occur when the genotype is homozygous for the normal sequence (e.g., wt/wt).

Thus, even if the probe does not hybridize with one sample (for example, pwt will not hybridize with a sample of genotype mt/mt), it might hybridize with another sample (e.g., pwt would hybridize to a degree, with a sample of genotype wt/mt).

For heterozygotes, the unknown will hybridize to a degree with both the normal (pwt) and mutant (pmt) probes. To determine heterozygosity, it is essential that both the probes are used for hybridization, one after the other.

Furthermore, if one wants to determine more than one genomic defect, one should be able to hybridize the immobilized unknown sample several times with different kinds of probes.

In accordance with another aspect of the invention, the nucleotide portion of the probe is an oligonucleotide with about 23 or even fewer nucleotides, and the sequence is such that it distinguishes between different sequences in the test samples characteristic of a particular genetic condition, e.g., sickle cell anemia, thalassemia or the like.

In carrying out the invention the unknown sample is encased in or sandwiched between layers of agarose. Accordingly, when the sample is ultimately contacted with the probe, the probe must penetrate the agarose to reach the nucleotide of the unknown and this slower contact might prevent unintended entrapment as opposed to binding by hybridization. In carrying out the invention, neither restriction enzyme digestion nor gel electrophoresis of the unknown sample is required prior to hybridization.

As a practical way of running multiple tests simultaneously, in place of a single depression in an agarose gel, the gel can be formed in such way as to provide multiple depressions, e.g., 96, into each of which a different unknown is placed. Then agarose solution is poured over the earlier gel and allowed to gel so as to encase all 96 unknowns. The entire gel can then be subjected to the labelled probe and each test portion read separately.

The initial agarose gel with multiple depressions can be formed by pouring agarose solution into a form, letting it gel into a sheet, placing a male mold member on top of the sheet with projections where depressions are desired, pouring additional agarose solution about the male mold member, allowing the additional solution to gel, and removing the male mold member.

The labelled probes employed in the hybridization step can be any known in the art, e.g., as described in Application Ser. No. 302,815, supra, and in Application Serial No. 438,642, filed Nov. 3, 1982, now abandoned, and refiled as Ser. No. 825,903, filed Feb. 4, 1986, now pending, the disclosures of which are incorporated herein by reference. As noted, however, relatively short oligonucleotide probes are suitable and preferred since they will move in and out of the agarose gel more quickly.

The invention will be further described in the following illustrative examples wherein all parts are by weight unless otherwise expressed.

EXAMPLE 1

(a) Preparation of agarose-encased sample

A horizontal gel tray (103 mm × 141 mm) is taped at both ends and placed on a level surface. An agarose solution (25 ml of 0.6% in TBE buffer) is poured into the tray and allowed to solidify. Additional agarose solution is added (same volume and percentage) and into the molten solution is placed the bottom of a flexible 96 well microtitre dish. This solution is also allowed to solidify. After removing the microtitre dish one is left with 96 wells. These wells can then be "loaded" with DNA (or RNA) solution consisting of an equal volume of DNA solution (12.5 μl) and 1.2% agarose. Once loaded the gel is then over layered with additional agarose solution (30 ml of 0.6%). When this solution has solidified the gel is then dried at 60° C. on a gel drier. The gel is then placed in 0.5N NaOH 0.15M NaCl, for 10 minutes to denature the DNA (omitted for RNA) then in 0.5M Tris-HCl pH8, 0.15M NaCl for 10 minutes and finally for 10 minutes in 6×SSC.

(b) Synthesis of Oligonucleotide Portion of Probe

Oligonucleotides were synthesized by the solid-phase phosphotriester method as described by Tan et al., Cold Spring Harbor Symp. Quant. Biol. 47 (1983) 383-91, on a Systec Microsyn 1450 automated DNA synthesizer. Oligonucleotides were purified by HPLC using a PRP-1 reverse phase column (Hamilton) and a linear gradient of 5-35% acetonitrile as described.

(c) Labeling of Probe

Oligonucleotides were labeled in a reaction that contained in 0.01 ml: 18.5 pmol DNA, 30 pmol $\gamma[^{32}P]$ATP (>5000 Ci/mmole, ICN), 50 mM Tris-Cl, pH 9, 10 mM $MgCl_2$, 10 mM dithiothreitol, 50 μg/ml bovine serum albumin and 6-8 units of T4 polynucleotide kinase. Reactions were incubated at 37° C. for 40 minutes. An equal volume of deionized 98% formamide containing 0.15% bromophenol blue and 0.15% xylene cyanole was added, the sample was heated for 5 minutes at 95° C. and then subjected to electrophoresis on a 14.5% acrylamide, 0.5% bisacrylamide gel containing 7M urea in 89 mM Tris-borate, pH 8.3, 2.5 mM EDTA (15 cm×30 cm×1 mm) Electrophoresis was continued until the bromophenol blue marker dye reached the bottom of the gel. The labeled oligonucleotide band was identified by autoradiography, the band was excised and the DNA was eluted by soaking the gel slice in two changes of 10 mM Tris-Cl, pH 8, 1 mM EDTA for at least 12 hours at 37° C.

(d) Hybridization of DNA in Gel

The dried gel was then hybridized with a labeled oligonucleotide (2×10⁶ cpm/ml) in 5×SSPE (SSPE=0.18 M NaCl, 10 mM ($Na_{1.5}PO_4$, 1mM $Na_2$EDTA, pH 7.0), 0.1% SDS and 10 μg/ml of sonicated, denatured E. coli DNA for 3 hours at 60° C. The dried gel was washed at room temperature in 6 X SSC (SSC=0.15M NaCl, 0.015 M sodium citrate) twice for 15 minutes followed by a third wash of at least 2 hours. The dried gel was then given a stringent wash for 1.5 minutes and occasionally followed by a second stringent wash of 1 minute. The stringent washes were done in 6×SSC and the temperature was dependent on the oligonucleotide used for the hybridization. The washed gel was then exposed to Kokak XAR-5 film with two Dupont Lightning-Plus intensifying screens at −70° C. for 1.5 to 3.5 days. Probes were washed from previously exposed gels by denaturing and neutralizing the gel as described above prior to the next hybridization. When hybridization occurs, the label is anchored to the gel and the film is exposed; thus the fact that the film is exposed is an indication of the presence of the test gene.

EXAMPLE 2

DNA from two mouse strains B10.BR and DBA-2 was tested in this simplified procedure for the presence or absence of the gene H-2K$^b$. B10.BR mice contain the H-2K$^b$ gene in the homozygous state while DBA-2 mice do not have this gene. DNA was prepared from the livers of these mice as described by Blin and Stafford (Nucl. Acids Res. 3:2303-2308, 1976). A DNA solution (0.2 ml at 800 μg/ml) was prepared for each type of DNA and the DNA was sheared by passing it several times through a 27 guage syringe needle. This solution was "loaded" into the walls of the gel as described in Example 1. Sequential wells were loaded with various dilutions of the DNA solution such that 10 Ng, 3 Ng, 1 Ng, 0.3 Ng and 0.1 ng was loaded for each DNA samples. The cloned H-2K$^b$ gene (Schulze, Pease, Obata, Nathenson, Reyes, Ikuta and Wallace, Mol. Cell. Biol. 3 750-755, 1983) was also loaded such that 30 ng, 10 ng, 3 ng, 1 ng, 0.3 ng, 0.1 ng, 0.03 ng, 0.01 ng were in consecutive wells. The gel was prepared for hybridization and hybridized with the radioactively label oligonucleotide 5' C.TGAGTCTCTCTGCTTCACCAGC 3' which is specific for H-2K$^b$ gene. Hybridization was performed as described in Example 1. The gel was washed in 6XSSC as described in Example 1 with the temperature of the stringent wash being 67° C. The gel was further washed 2X for 5 minutes in 6XSSC at 67° C. and finally exposed to X-ray film. The presence of the H-2K$^b$ gene is indicated by the hybridization of the probe to the B10.BR sample but not to the DBA-2 sample, evidenced by exposure or non-exposure of the X-ray film due to the presence of the radioactive label when specific hybridization took place.

EXAMPLE 3

A loaded gel is prepared as described in Example 1. The loaded gel is then placed in 500 ml methanol for 1 hour, the methanol is removed and replaced by another 500 ml methanol. The gel is left in the methanol overnight and then dried on a gel drier. The gel is then placed in 0.5N NaOH, 0.15M NaCl for 10 minutes and then in 0.5M Tris-HCl pH 8, 0.15M NaCl for 10 minutes and finally in 6×SSC for 10 minutes. The gel is then hybridized as described above. The advantage of this procedure is that it provides increased sensitivity for the detection of complementary sequences.

It will be understood that the specification and examples are illustrative but not limitative of the present invention and that other embodiments within the spirit and scope of the invention will suggest themselves to those skilled in the art.

I claim:

1. A process for the detection of a particular polynucleotide sequence in a polynucleotide-containing test sample consisting essentially of forming an agarose gel having a depression therein, adding the test sample to said depression, putting agarose solution in the depression and permitting it to gel thereby encasing the test sample in agarose gel, denturing the polynucleotide in the test sample within the agarose gel, contacting the test sample-containing gel with an oligonucleotide or polynucleotide probe having a sequence complementary with a sequence for which the sample is being tested under hybridization conditions, said probe having at least 23 nucleotides, said probe carrying a readable label, and determining the extent of hybridization, the extent of hybridization being determined by reading the label and, wherein after hybridization the gel is washed to remove non-hybridized probe.

2. A proces according to claim 1, wherein the hybridization is conducted in 5×SSPE, wherein SSPE comprises 0.18M NaCl, 10 mM, $(Na_{1.5})$ $PO_4$, 1 mM $Na_2EDTA$, pH of 7.0, 0.1% SDS and 10 μg/m; of sonicated, denatured *E. coli* DNA for 3 hours at 60° C.

3. A process according to claim 1 wherein the label is a radioactive isotope.

4. A process according to claim 1 wherein the label is biotin.

5. A process according to claim 1, wherein the encased test sample is dried prior to denaturing.

6. A process according to claim 1, wherein the probe is an oligonucleotide.

7. A process according to claim 1, wherein the probe is a polynucleotide sequence which distinguishes between different sequences in test samples from individuals suspected of having a particular genetic condition.

8. A process according to claim 7, wherein the genetic condition is sickle cell anemia.

9. A process according to claim 7, wherein the genetic condition is thalassemia.

* * * * *

UNITED STATES PATENT AND TRADEMARK OFFICE
CERTIFICATE OF CORRECTION

PATENT NO. : 4,767,700
DATED : August 30, 1988
INVENTOR(S) : R. Bruce Wallace

It is certified that error appears in the above-identified patent and that said Letters Patent is hereby corrected as shown below:

| | |
|---|---|
| Col. 4, line 33 | After "loaded into the" delete "walls" and substitute --wells-- |
| Col. 4, lines 35-36 | Delete "10 Ng, 3 Ng, 1 Ng, 0.3 Ng and 0.1 ng" and substitute -- 10 μg, 3 μg, 1 μg, 0.3 μg and 0.1 μg-- |
| Col. 4, line 43 | Delete "C.T" and substitute --CT-- |
| Col. 5, line 15 | Delete "denturing" and substitute --denaturing-- |

Signed and Sealed this

Twenty-eighth Day of March, 1989

Attest:

DONALD J. QUIGG

Attesting Officer

Commissioner of Patents and Trademarks